United States Patent
Cai et al.

(10) Patent No.: US 12,180,273 B2
(45) Date of Patent: Dec. 31, 2024

(54) ANTI-GIANT PANDA LIF MONOCLONAL ANTIBODY, AND HYBRIDOMA CELL LINE, AND USE THEREOF

(71) Applicant: Chengdu Research Base of Giant Panda Breeding, Chengdu (CN)

(72) Inventors: Kailai Cai, Chengdu (CN); Rong Hou, Chengdu (CN); Yuliang Liu, Chengdu (CN); Jingchao Lan, Chengdu (CN); Mengshi Zhang, Chengdu (CN); Feiping Li, Chengdu (CN); Shenfei Wang, Chengdu (CN); Xianbiao Hu, Chengdu (CN); Juan Wang, Chengdu (CN); Mingyue Zhang, Chengdu (CN)

(73) Assignee: Chengdu Research Base of Giant Panda Breeding, Chengdu (CN)

( * ) Notice: Subject to any disclaimer, the term of this patent is extended or adjusted under 35 U.S.C. 154(b) by 0 days.

(21) Appl. No.: 18/610,618

(22) Filed: Mar. 20, 2024

(65) Prior Publication Data

US 2024/0383977 A1    Nov. 21, 2024

(30) Foreign Application Priority Data

May 16, 2023 (CN) .......................... 202310546376.1

(51) Int. Cl.
*C07K 16/24* (2006.01)

(52) U.S. Cl.
CPC ........ *C07K 16/244* (2013.01); *C07K 2317/14* (2013.01)

(58) Field of Classification Search
CPC ........... C07K 16/24; C12N 15/00; C12N 5/12
See application file for complete search history.

*Primary Examiner* — Dong Jiang
(74) *Attorney, Agent, or Firm* — Birchwood IP

(57) ABSTRACT

The present invention discloses an anti-giant panda LIF monoclonal antibody, a hybridoma cell line, and use thereof, and belongs to the field of biotechnology. The antibody comprises a heavy chain variable region having an amino acid sequence set forth in SEQ ID NO. 1 and a light chain variable region having an amino acid sequence set forth in SEQ ID NO. 2. The hybridoma cell line LIF-2 is deposited at China Center for Type Culture Collection on Oct. 28, 2021 with the accession number of CCTCC NO: C202171. The anti-giant panda LIF monoclonal antibody developed by the present invention can accurately identify the target protein LIF, and lays an important foundation for LIF protein localization, tissue expression information, study on LIF and a receptor and a target cell thereof by using the high-specificity LIF monoclonal antibody and exploration of the effect of LIF in embryonic diapause in giant pandas.

4 Claims, 1 Drawing Sheet

Specification includes a Sequence Listing.

ANTI-GIANT PANDA LIF MONOCLONAL ANTIBODY, AND HYBRIDOMA CELL LINE, AND USE THEREOF

CROSS-REFERENCE TO RELATED APPLICATIONS

This application claims priority to Chinese Patent Application No. 202310546376.1, filed on May 16, 2023, which is hereby incorporated by reference in its entirety.

TECHNICAL FIELD

The present invention belongs to the field of biotechnology, and specifically relates to an anti-giant panda LIF monoclonal antibody, a hybridoma cell line, and use thereof.

SEQUENCE LISTING

The present application contains a sequence listing which was filed electronically in XML format and is hereby incorporated by reference in its entirety. Besides, the XML copy is created on Jun. 4, 2024, is named "ANTI-GIANT PANDA LIF MONOCLONAL ANTIBODY, HYBRIDOMA CELL LINE, AND USE THEREOF-Sequence Listing" and is 8,999 bytes in sizes.

BACKGROUND

Embryonic diapause is a physiological phenomenon in which the embryo is in a dormant state after the embryo develops to a blastocyst stage, that is, the cell proliferation is stopped, and the embryo can be activated to restart development and implantation when the internal and external environment is suitable. At present, embryonic diapause has been found in the embryonic development of more than 130 species of animals, and it has been determined that the embryonic diapause is found in eight known species of bears, including giant pandas. Embryonic diapause is regulated by the external environment and factors secreted by pituitary gland, ovary and uterus, and the main influence factors are as follows: (1) prolactin; (2) estrogen; (3) progestogen; (4) leukemia inhibitory factor (LIF); (5) vascular endothelial growth factor (VEGF); (6) microRNA; (7) epidermal growth factor (EGF) and the like.

LIF is a paracrine factor secreted by the endometrial gland epithelium under estrogen stimulation, is a member of the interleukin-6 family, and plays an important role in the adhesion and invasion stages of embryo implantation. The study shows that the expression of LIF mRNA changes with the female menstrual cycle, wherein the expression of LIF mRNA is low in the proliferative phase, the transcription expression significantly increases after the LIF mRNA enters the mid-secretory phase, and the LIF mRNA content reaches a peak in the mid-to-late secretory phase. This change is consistent with the implantation window period. In other phases of the menstrual cycle, LIF shows no expression or only trace expression. Meanwhile, LIF is indispensable to the establishment of endometrial receptivity. LIF gene-deficient mice can become pregnant, but their blastocysts cannot complete implantation and development. However, blastocysts transplanted into normal pseudopregnant mice can develop smoothly until birth. Studies in other mammals including rabbits, pigs, cattle and the like have shown similar results.

At present, the deficiency of LIF-specific antibodies in giant pandas results in insufficient studies on LIF in giant pandas. Therefore, the construction of the high-specificity LIF monoclonal antibody for giant pandas and the application of the LIF monoclonal antibody in Western Blot detection lay an important foundation for LIF protein localization, tissue expression information, study on LIF and a receptor and a target cell thereof by using the high-specificity LIF monoclonal antibody and exploration of the effect of LIF in embryonic diapause in giant pandas.

SUMMARY

Aiming at the defects in the prior art, the present invention provides an anti-giant panda LIF monoclonal antibody, a hybridoma cell line, and use thereof, which can effectively solve the lack of a specific anti-giant panda LIF-specific antibody in the prior art.

To achieve the above objective, the technical solutions used by the present invention to solve the technical problems are as follows.

An anti-giant panda LIF monoclonal antibody comprises a heavy chain variable region having an amino acid sequence set forth in SEQ ID NO. 1 and a light chain variable region having an amino acid sequence set forth in SEQ ID NO. 2, wherein a complete sequence of the light chain is set forth in SEQ ID NO. 5 and a complete sequence of the heavy chain is set forth in SEQ ID NO. 6.

Further, the amino acid sequence of the heavy chain variable region is an amino acid sequence that has no less than 80% homology to a sequence set forth in SEQ ID NO. 1 and has the same function; and
    the amino acid sequence of the light chain variable region is an amino acid sequence that has no less than 80% homology to a sequence set forth in SEQ ID NO. 2 and has the same function.

Further, a nucleotide sequence coding the heavy chain variable region is set forth in SEQ ID NO. 3, and a nucleotide sequence coding the light chain variable region is set forth in SEQ ID NO. 4.

Further, a subtype of the anti-giant panda LIF monoclonal antibody is IgG2b.

An expression vector comprises the anti-giant panda LIF monoclonal antibody.

A hybridoma cell line LIF-2 secreting the anti-giant panda LIF monoclonal antibody is deposited at China Center for Type Culture Collection (CCTCC) on Oct. 28, 2021 with the accession number of CCTCC NO: C202171 and the depository address of Wuhan University, Wuhan, China.

Use of the anti-giant panda LIF monoclonal antibody in the detection of a leukemia inhibitory factor.

Further, Western Blot is used for detection.

Use of the anti-giant panda LIF monoclonal antibody in the preparation of a Western Blot detection kit for detecting a giant panda leukemia inhibitory factor.

A preparation method for the anti-giant panda LIF monoclonal antibody comprises the following steps:
    (1) performing prokaryotic expression of an amino acid sequence of a giant panda LIF (23-202), wherein specific sequence information is as follows: SPLPITPVNATCATRHPCHSNLMNQIRNQLAQLNG-SANALFILYYTAQGEPFPNNLDKL CGPNVTDFPPFHANGTERTRLVELYRLIAYL-GASLGNITRDQKVLNPNALSLHSKLNATADIMR-GLLSNVLCRLCNKYH-VAHVDVAYGPDTSGKDVFQKKKLGCQLLGKY-KQVIA VVAQAF, as immunogen LIF (23-202) for producing a specific antibody;

(2) immunizing a mouse with the immunogen LIF (23-202) prepared in the step (1);
(3) performing cell fusion to obtain a giant panda LIF monoclonal antibody hybridoma cell line LIF-2; and
(4) expanding culture, and purifying a supernatant of a culture medium to obtain the anti-giant panda LIF monoclonal antibody.

The beneficial effects of the present invention are as follows.

The present invention establishes a hybridoma cell line secreting the anti-LIF monoclonal antibody by cell fusion, obtains the high-specificity LIF monoclonal antibody, establishes the high-specificity LIF monoclonal antibody to be applied to Western Blot detection, and lays an important foundation for LIF protein localization, tissue expression information, study on LIF and a receptor and a target cell thereof by using the high-specificity LIF monoclonal antibody and exploration of the effect of LIF in embryonic diapause in giant pandas.

DESCRIPTION OF EMBODIMENTS

The following description of the specific embodiments of the present invention is provided to facilitate the understanding of the present invention by those skilled in the art, however, it should be understood that the present invention is not limited to the scope of the specific embodiments, and for those of ordinary skill in the art, various changes that are made without departing from the spirit and scope of the present invention as defined and determined by the appended claims are apparent, and all inventions and creations that are made by using the concept of the present invention are within the protective scope.

In the present invention, SDS-PAGE refers to sodium dodecyl sulfate polyacrylamide gel electrophoresis, and can separate proteins in a sample according to protein molecular weight.

In the present invention, ELISA refers to enzyme-linked immunosorbent assay.

In the invention, the HT culture medium refers to a nucleoside mixture adopting hypoxanthine and thymidine, and is mainly used for hybridoma cells and cell culture.

EXAMPLE 1. PREPARATION OF ANTI-GIANT PANDA LIF MONOCLONAL ANTIBODY

1. Preparation of Immunogen 1.1 Preparation of LIF (23-202) Recombinant Plasmid

According to NCBI database, an amino acid sequence of a giant panda LIF, with an accession No. XP_011218489.1, is as follows:

MKVLAAGVVPLLLVLHWKHGAGSPLPITPVNAT-CATRHPCHSNLMNQIRN QLAQLNGSANALFI-LYYTAQGEPFPNNLDKLCGPNVTDFPPFHANG-TERTRLVELYRLI AYLGASLGNITRDQKVLNPNALSLHSKLNAT-ADIMRGLLSNVLCRLCNKYHVAHVDV AYGPDTSGKDVFQKKKLGCQLLGKYKQVIA-VVAQAF (SEQ ID NO. 7), and has a total of 202 amino acids. To obtain a specific immunogen, the LIF (23-202) recombinant protein expression vector expressing the amino acid sequence of LIF protein 23-202 was constructed by prokaryotic expression. LIF (23-202) gene was inserted into expression vector pET30a using whole gene synthesis and by restriction enzyme sites NdeI and HindIII, and the accuracy of the final expression vector was confirmed by enzyme digestion and sequencing.

Figure 1:
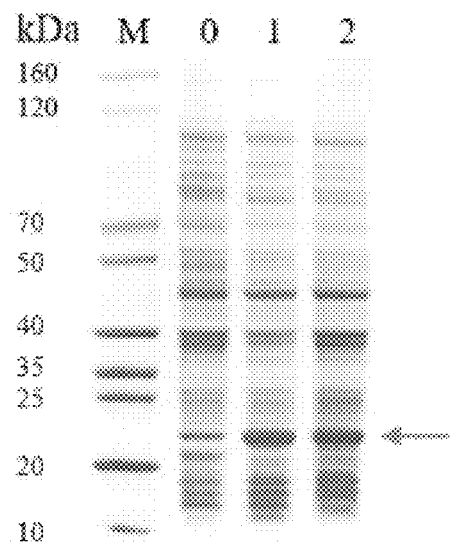
FIG. 1 is a diagram showing expression results of LIF (23-202) protein analyzed by SDS-PAGE; wherein band M: SDS-PAGE Protein Marker; band 0: Control (without IPTG); band 1: induced at 15° C. for 16 h; band 2: induced at 37° C. for 16 h.

1.2 LIF (23-202) Protein Expression and Identification (1) The constructed plasmid containing the LIF (23-202) gene was transformed into BL21 (DE3) competent cells, which were then uniformly coated on an LB plate (containing 50 μg/mL of kanamycin sulfate), followed by being placed upside down in an incubator at 37° C. overnight.
(2) A monoclone was selected from the transformed plate, inoculated into 4 mL of LB medium (containing 50 μg/mL of kanamycin sulfate), and cultured until OD600 was 0.5-0.8; and a culture medium in a test tube was added with IPTG at a final concentration of 0.2 mM and then placed at 15° C. and 37° C. to induce expression.
(3) The induced culture medium was centrifuged at 12000 rpm for 5 min, the supernatant was removed, the PBS solution was added to resuspend the pellets, SDS-PAGE sample buffer was added, a sample was heated at 100° C. for 10 min and centrifuged, and the supernatant was collected for electrophoresis. 160 V voltage-stabilized electrophoresis was performed until a bromophenol blue band moved to a position 1 cm away from the bottom of the gel, and the gel was taken out, dyed and decolored by using a protein gel rapid treatment system. The results are shown in FIG. 1.
(4) The culture was expanded, and after the cells were grown until OD600=0.8, the cells were induced at 15° C. for 16 h with the addition of IPTG at a final concentration of 0.2 mM and then collected.

1.3 LIF (23-202) Protein Purification

Figure 2:
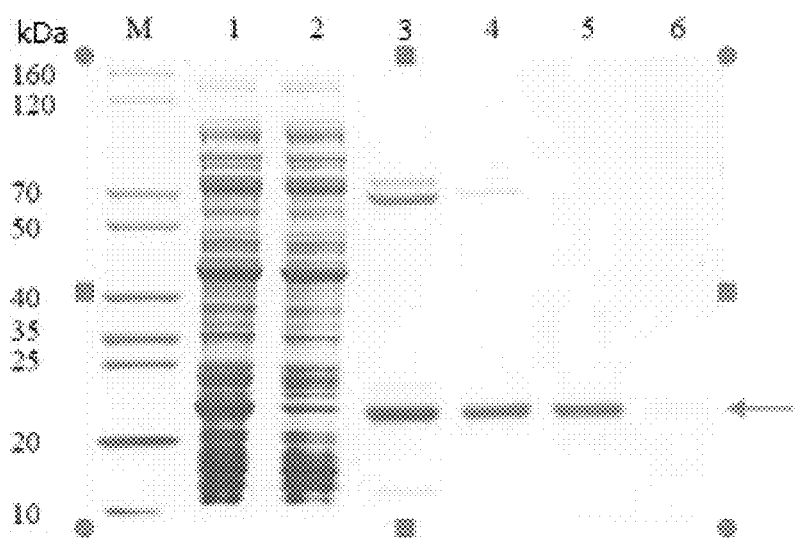
FIG. 2 is a diagram showing results of the supernatant purification of LIF (23-202) protein in inclusion bodies analyzed by SDS-PAGE; wherein band M: SDS-PAGE Protein Marker; band 1: supernatant after centrifugation of whole bacteria; band 2: an effluent after the supernatant is incubated with Ni-IDA; bands 3-5: elution fractions of 50 mM Imidazole; and band 6: elution fraction of 100 mM Imidazole.

The whole bacteria were sonicated with 50 mM Tris (pH 8.0), 300 mM NaCl, 20 mM Imidazole containing 1% Triton X-100, 1 mM dithiothreitol (DTT) and 1 mM phenylmethylsulfonyl fluoride (PMSF) while the Ni-IDA affinity column was equilibrated with 50 mM Tris (pH 8.0), 300 mM NaCl and 20 mM Imidazole buffer, then the target protein was eluted with different concentrations of imidazole in the equilibration buffer, and each eluted fraction was collected for SDS-PAGE analysis and examined. The analysis results are shown in FIG. 2.

Purification was performed through Ni-IDA affinity chromatography. Band 5 with a relatively high purity concentration was collected and dialyzed into 1×PBS (pH 7.4). After dialysis, this band was filtered with a 0.22 μm filter and aliquoted and frozen at −80° C.

1.3 Immunization of Mice by Antigen

A mixture of adjuvant:antigen=1:1 was used for vaccination (if an amount of antigen is insufficient, the antigen can be mixed with sodium chloride and then emulsified with the adjuvant). The first immunization was performed with Freund's complete adjuvant, and the subsequent immunization was performed with Freund's incomplete adjuvant. Steriled syringes, three-way tubes and disposable syringes were prepared prior to immunization. The antigen and NaCl were firstly aspirated into a syringe by the sterilized syringe (a total of 400 μL, a volume of four mice), then the adjuvant was aspirated into the syringe by the sterilized syringe (a total of 400 μL, a volume of four mice), the sterilized syringe was connected in the three-way tube for emulsification (the emulsification was performed for about more than 10 minutes until the mixture was in a water-in-oil state), and finally the fused mixed solution was transferred into a disposable syringe for injection.

Day 1: intraperitoneal, 200 μL for one mouse. (Antigen amount was 100 μg/mouse)
Day 14: intraperitoneal, 200 μL for one mouse. (Thereafter, the antigen amount was 50 μg/mouse)
Day 21: intraperitoneal, 200 μL for one mouse.
Day 27: intraperitoneal, 200 μL for one mouse.

3 to 4 days after the third immunization, blood was collected from the tail of the mouse and centrifuged at 12000 rmp for 8 min, and the serum was taken to determine the titer. The LIF (23-202) protein with a coating concentration of 20 ng/mL was used as the antigen, and the serum titer was detected by ELISA. Once the titer of the serum reaches the standard, fusion can be prepared. If the titer of the serum is not high enough, immunization needs to continue until the titer reaches the standard. The immune serum titers are shown in Table 1:

TABLE 1

Immune serum titers

| Serum dilution ratio | Mouse No. 1 | Mouse No. 4 | Mouse No. 6 |
| --- | --- | --- | --- |
| 1:1000 | 2.163 | 2.207 | 2.580 |
| 1:2000 | 1.993 | 1.856 | 2.613 |
| 1:4000 | 1.566 | 1.458 | 2.446 |
| 1:8000 | 1.122 | 1.252 | 2.350 |
| 1:16000 | 0.768 | 0.782 | 2.166 |
| 1:32000 | 0.505 | 0.487 | 1.661 |
| 1:64000 | 0.319 | 0.293 | 0.972 |
| Negative control | 0.058 | 0.064 | 0.061 |

The results indicate that mice Nos. 1, 4, and 6 meet the immune requirements and can be used for cell fusion experiments.

1.4 Cell Fusion

1.4.1 Recovery of Myeloma Cells (SP2)

The cryopreserved cells were first taken out from liquid nitrogen and quickly thawed in a 37° C. water bath to loosen the cells. The cells were then put into a 15 mL centrifuge tube and then mixed well with about 5 mL of PBS, the mixture was centrifuged at 1000 rpm for 5 min, the supernatant was discarded, and the SP2 cells were washed twice. The cells were cultured in a culture flask, marked, and finally placed in an incubator at 37° C. with 5% CO2.

1.4.2 Passages of SP2 Cells

When the cells in the culture flask covered about 80% of the bottom of the flask, the cell passage was performed. The cells were pipetted down with a pipette tip, the culture medium was aspirated into a 15 mL centrifuge tube and centrifuged at 1000 r/min for 5 min, the supernatant was discarded, 5 mL of PBS was added, mixed well by pipetting and centrifuged again to discard the supernatant, and the PBS washing was repeated twice. After washing, 2 mL of a 10% complete culture medium was added to resuspend the cells, and a proper amount of the cells were taken into a culture flask and cultured in a carbon dioxide incubator.

1.4.3 Preparation of Trophoblast Macrophages (Prepared the Day Before Fusion)

Mice were killed by cervical vertebrae dislocation. It should be noted that when the cervical vertebrae is cut off, the compression on the abdominal cavity is minimized to avoid damaging the blood vessel in the abdominal cavity so as to prevent the feeder cells from containing a large number of blood cells. The mice were soaked in 75% alcohol for 5 min, and then the tails of the mice were held by hand and rinsed in alcohol up and down several times. The mice were placed in a sterile plate. The skin was cut off from the back abdomen with sterile scissors, and two sides of the skin were torn open by hand to expose the abdomen. It should be noted not to damage the peritoneum. The peritoneum was wiped with an alcohol cotton swab. The incomplete culture medium containing double antibody (double antibody: incomplete culture medium=1:100) was aspirated by a syringe (6-8 mL) and injected into the abdominal cavity, and the peritoneum was carefully lifted by forceps during injection to avoid the needle from sticking to the abdominal organs such as the intestinal canal. The abdomen was gently massaged with a cotton ball for one minute, and the injected culture medium was aspirated and transferred to a centrifuge tube. The culture medium was centrifuged at 1000 r/min for 5 min, and the supernatant was discarded. The culture medium was washed with PBS four times. The cells were resuspended in a 10% complete culture medium.

The cell suspension was added to a 96-well plate at 100 μL/well, and the 96-well plate was cultured in a CO2 incubator. (It is not advisable to have too many macrophages, and some of the collected cells may be discarded as appropriate.)

1.4.4 Preparation of Immune Splenocytes (1) Obtaining Mouse Spleen

The mice that meet the immune requirements were taken. First, aseptic operation is ensured to prevent cell contamination. After the mice were sacrificed, the mice were soaked in 75% alcohol for about five minutes, placed in a sterile plate, specifically placed in a position convenient for operation (an ultra-clean bench), and dissected. The tail of the mice was cut into a small opening by scissors, the fur layer were cut open by hands, the cut part was lightly wiped by an alcohol cotton swab, the semitransparent film covering the internal organs was picked up by forceps and was cut open, the spleen was exposed, the spleen was taken out lightly, the fat tissue on the spleen was removed as much as possible, and the taken-out spleen was placed in PBS for washing.

(2) Preparation of Spleen Cell Suspension

The spleen was washed with PBS and rinsed about 3 times. The spleen was placed in a plate. The spleen was chopped as much as possible with scissors. PBS was added for washing and filtering. The tissue cells were discarded. The isolated spleen cell suspension was collected and centrifuged at 1000 r/min for 5 min, and the supernatant was discarded. The cell suspension was washed with 5 mL of PBS and centrifuged at 1000 r/min for 5 min, and this step was repeated three times. After washing, 2 mL of incomplete culture medium (DMEM) was added to resuspend the cells. The cell suspension was diluted 100 times or 1000 times for cell counting, and the remaining cells were placed in a 37° C. water bath for later use.

(3) Preparation of SP2 cell suspension: sucking cell fluid by a rubber-tipped pipette, blowing a film (cells were suspended or grown adherently) at the bottom of a culture bottle, transferring the cell fluid into a 15 mL centrifuge tube by a pipettor, and centrifuging at 1000 r/min for 5 min; and discarding the supernatant, adding 5 mL of PBS, mixing uniformly, centrifuging at 1000 r/min for 5 min, repeatedly washing twice, adding 2 mL of incomplete culture medium (DMEM) to resuspend the cells after washing, diluting the cell suspension by 100 times or 1000 times for cell counting, and placing the remaining cells in a 37° C. water bath for later use.

1.4.5 Cell Fusion Under the Action of PEG

SP2 was mixed with splenocytes at a ratio of 1:4 (between 1:10 and 1:4), and the mixture was centrifuged at 600 rpm for 3 min; and the supernatant was discarded. The bottom of the centrifuge tube was flicked slightly to loosen the cell pellet. 0.6 mL of 50% PEG solution preheated to 37° C. was slowly added over 1 min with gentle shaking and tapping. The centrifuge tube was left to stand 1 min after the addition. 10 mL of the preheated incomplete culture medium at 37° C. was used to stop the PEG action, the incomplete culture medium was dropwise added and tapped with rotating the centrifuge tube and added at a constant speed. The centrifuge tube was left to stand for 2 min after the addition was completed. The culture medium was centrifuged at 800 rpm for 5 min, and the supernatant was discarded; and PBS or incomplete culture medium was used to wash twice to remove PEG.

After washing, the supernatant was discarded and the cells were resuspended in 10 mL of histone acetylase (HAT) selection culture medium. The above cells were added to a 96-well plate with a feeder cell layer (the previously prepared macrophage plate was used, the liquid in the well was aspirated and discarded first and then washed once with incomplete culture medium, and the remaining liquid was aspirated), and 100 µL was added to each well; and the culture plate was placed in a CO2 incubator for culture. After 4 h, complete culture medium containing HAT (19.6 mL 10% complete culture medium+0.4 mL HAT) was added to the wells, and 100 µL was added to each well; and the culture plate was placed in a CO2 incubator for culture.

1.4.6 Selection Culture (1) Exchanging HAT culture medium by a half-liquid method on the fourth day of fusion culture: aspirating 100 µL of the supernatant from each well of the 96-well plate by a pipettor, discarding, adding 100 µL of HAT culture medium (HAT culture medium prepared to be 10% complete culture medium: HAT=1:50) to each well, and adding 200 µL of 50×HAT to 10 mL of complete culture medium per plate.

(2) Exchanging HT culture medium by a half-liquid method on the seventh day of fusion culture: aspirating 100 µL of the supernatant from each well of the 96-well plate by a pipettor, discarding, adding 100 µL of HT culture medium (HT culture medium prepared to be 10% complete culture medium: HT=1:50) to each well, and adding 200 µL of 50×HT to 10 mL of complete culture medium per plate.

1.4.7 Positive Clone Screening

Obvious clone cells can be seen in the wells after about 7 days of culture. When the clone cells have grown enough (about day 12), the culture medium can be aspirated to detect whether the clone cells secrete antibodies.

(1) The previously coated corresponding ELISA (coated with LIF (23-202) at a concentration of 20 ng/ml) was removed from the freezer and allowed to return to room temperature, 100 µL of the to-be-tested culture medium was added to each well in the plate, two wells served as negative and positive controls, 10% culture medium for negative controls and 10000-fold diluted serum for positive controls (serum collected from mouse orbits before fusion).

(2) Incubation: the plate was sealed with a sealing plate film and incubated in a 37° C. incubator for 1 h.

(3) Washing: the sealing plate film was carefully removed, the plate was washed for 4 times, and the water was drained as much as possible.

(4) Adding double antibody: the double antibody was diluted 10000 times, 50 µL per well.

(5) Incubation: the plate was sealed with a sealing plate film and incubated at 37° C. for 30 min.

(6) Washing: the sealing plate film was carefully removed, the plate was washed for 4 times, and the water was drained as much as possible.

(7) Color development: 100 µL of color development agent TMB was added into each well, gently shaken for uniformly mixing, and developed for about 10 min in an incubator.

(8) Colorimetric determination: 50 µL of stop solution was added to each well (stop solution=making up 21.5 mL concentrated sulfuric acid to 200 mL) and gently shaken for uniformly mixing; the wavelength of a microplate reader was set to 450 nm, and the value of each well was determined.

The wells with the highest positive results (at least 4 times that of the negative control) were selected as positive clone wells.

1.4.8 Screening of Anti-Giant Panda LIF Monoclonal Antibody Hybridoma Cell Line by Limiting Dilution (1) Counting of positive well cells: the positive cloning wells obtained by screening were subjected to limiting dilution. The cells in the wells was transferred into a 15 mL centrifuge tube (rotating while blowing to suspend the cells), and 10% of complete culture medium was supplemented to 2 mL; the cell fluid containing only 1000 cells was counted by the counting plate and then used for the next experiment (since only one cell was needed for 1 well, about 100 cells were needed for one 96-well plate, and 1000 cells were needed for 10 plates).

(2) The cell fluid was added into 200 mL of complete culture medium and mixed well, and sampling was performed in 96-well plate at 200 µL/well for a total of ten 96-well plates.

(3) Finally, the culture plate was placed in a CO2 incubator for culture.
(4) After 4-5 days of culture, small cell clones were visualized on an inverted microscope, the growth of the cells was observed, and wells where single cells were grown together were recorded.
(5) On day 5 of culture, the solution in the wells with recorded single cell growth and aggregation was exchanged, and a 10% complete culture medium was added at 100 μL/well.
(6) On day 8 to day 9 of culture, cell clones were visually observed and subjected to antibody detection in time, and the wells in which single cells grow and aggregate and the wells with better growth conditions were subjected to culture medium test (ELSIA test). The wells with strong positive results are the anti-giant panda LIF monoclonal antibody hybridoma cell lines. According to the present invention, 5 positive hybridoma cell lines are finally obtained and are respectively named as LIF-1, LIF-2, LIF-3, LIF-4 and LIF-5.

1.4.9 Subtype Identification

Subtype identification was performed using Pierce Rapid ELISA Mouse mAb Isotyping Kit (37503).

Preparation: TBS in the kit was dissolved in 500 mL double distilled water for diluting a sample, 870 mL double distilled water was mixed with 30 mL 30× Wash Buffer uniformly for washing a plate, the number of plates needed was determined according to the amount of the sample, the remaining plates were put back into a refrigerator at 4° C. for storage, 450 μL of sample diluent was prepared, 20 μL of cell culture medium was aspirated, and 980 μL of TBS was added for mixing uniformly.

Experimental steps: the plate was balanced to the room temperature, a to-be tested sample was added into each well at 50 μL/well, wherein one sample needs to be added to 8 wells, i.e., one strip, 50 μL/well of Goat Anti-Mouse Immunoglobulin G (IgG)+Immunoglobulin A (IgA)+Immunoglobulin M (IgM)·Horseradish Peroxidase (HRP) was added, the plate was gently shaken and mixed, covered with a sealing plate film, incubated at room temperature for one hour, washed 4 times and drained. 75 μL/well of TMB chromogenic solution was added to develop color, and the liquid in the well turned blue. After 5-15 min of color development, 75 μL/well of stop solution was added to stop the reaction, and the liquid changed from blue to yellow. The results of the anti-giant panda LIF monoclonal antibody hybridoma cell lines identified and screened are shown in Table 2, wherein antibody subtypes secreted by LIF-1, LIF-2, LIF-4 and LIF-5 are IgG2b types, and antibody subtype secreted by LIF-3 is IgG2a type.

TABLE 2

Subtypes of hybridoma cell lines

| OD value | IgG1 | IgG2a | IgG2b | IgG3 | IgA |
|---|---|---|---|---|---|
| LIF-1 | 0.024 | 0.022 | 0.305 | 0.017 | 0.021 |
| LIF-2 | 0.019 | 0.021 | 0.425 | 0.018 | 0.019 |
| LIF-3 | 0.024 | 0.260 | 0.022 | 0.024 | 0.020 |
| LIF-4 | 0.025 | 0.020 | 0.334 | 0.018 | 0.020 |
| LIF-5 | 0.031 | 0.033 | 0.336 | 0.026 | 0.027 |

1.4.10 Expanded Culture, Purification and Concentration of Monoclonal Antibodies (1) Batch culture: the cell wells in which the subtype was identified and the monoclonal antibody was obtained were transferred to a 24-well plate (cell suspension was performed by pipetting while rotating, and complete transfer was performed), and 600 μL of a 10% complete culture medium was added for culture.
(2) The growth of the cells was observed, after a relatively large number of cells had grown, titer determination was performed, and cells having a high titer were transferred to a small culture flask and cultured (cells were first blown out from a 24-well plate to suspend the cells, the cells were transferred to the culture flask with a pipettor, and 7 mL of a 10% complete culture medium was added).
(3) The growth condition of the cells was observed, the cells were transferred to a large culture flask for culture after the cells were grown well. One small culture flask was transferred to two large culture flasks for culture (cell passaging).
(4) A plurality of culture flasks were transferred for culture, a part of cells were cryopreserved, and then the culture medium was taken for purifying the antibody through a column. The column was filled with Pierce Protein G Agarose, and the purified anti-giant panda LIF monoclonal antibody was concentrated using a 10000 kda ultrafiltration tube and stored at −20° C. for use.

1.4.11 Cryopreservation of Monoclonal Antibody Cell Lines

After the 5 identified giant panda LIF monoclonal antibody hybridoma cell lines were cultured stably, the cells in the culture flask were blown out to suspend the cells in the culture medium (the cells were generally suspended in the culture medium or grown adherently), and then the cells were transferred to a 15 mL centrifuge tube. The cells were centrifuged at 1000 rpm/5 min. PBS washing twice: the supernatant in the centrifuge tube was aspirated and discarded, the centrifuge tube was added with PBS, mixed evenly and centrifuged for 1000 rpm/5 min, and these operations were repeated for the last time. Finally, the supernatant was aspirated with a pipettor, and a suitable amount of the cryopreservation solution (cryopreservation solution=5 mL serum+4 mL DMEM+1 mL DMSO, reversed for mixing well, and filtered for use) was added to the cells and mixed. Finally, the cell fluid was added to the cryopreservation tube, with 1 mL of cell fluid in each tube. The cryopreservation tube was placed in a cryopreservation box and placed at −80° C. overnight, and then the cell lines were placed in liquid nitrogen for long-term storage.

EXAMPLE 2. DETERMINATION OF TITER OF ANTI-GIANT PANDA LIF MONOCLONAL ANTIBODY AND APPLICATION THEREOF IN WESTERN BLOT TECHNOLOGY

1. Application of Anti-Giant Panda LIF Monoclonal Antibody in Western Blot Technology (1) Extraction of Total Protein of Target Cells Application of the protein extraction kit: C510004-0020, available from Sangon Biotech (Shanghai) Co., Ltd., extracted total protein of bone marrow mesenchymal stem cells of giant pandas, and measured for total protein concentration by BCA method.

(2) Gel preparation: preparing polyacrylamide gel, 5% of concentrated gel and 12% of separation gel.

Figure 3:
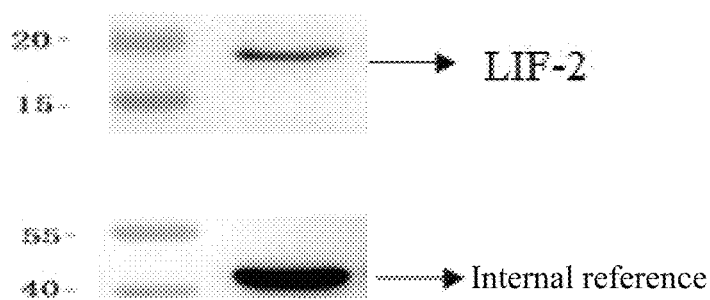
FIG. 3 is a diagram showing results of Western-blot detection of a giant panda LIF monoclonal antibody.

(3) Sample preparation: the protein loading was 80 μg.
(4) Electrophoresis: the concentrated gel was subjected to electrophoresis at 80 V for 30 min, and the separation gel was subjected to electrophoresis at 120 V for 90 min.
(5) Film transferring: 250 mA, 40 min.
(6) Blocking: 5% skim milk, slowly shaking at 37° C. for 2 h.
(7) Incubation of primary antibody: the antibodies of hybridoma cell lines LIF-1, LIF-2, LIF-3, LIF-4 and LIF-5 and the internal reference antibody of GAPDH were diluted at a ratio of 1:1000, slowly shaken at 4° C. overnight, and rewarmed at 37° C. for 1 h the next day.
(8) Incubation of secondary antibody: dilution at 1:8000, and incubation for 1 h at 37° C.
(9) ECL exposure and western blot detection are shown in FIG. 3.

The Western blot results show that only LIF-2 has a specific target band, which can be used in the application of western blot technology, and then the obtained hybridoma cell line LIF-2 is deposited at China Center for Type Culture Collection on Oct. 28, 2021 with the accession number of CCTCC NO: C202171 and the depository address of Wuhan University, Wuhan, China.

2. Titer Determination and Sequence Determination of Anti-Giant Panda LIF-2 Monoclonal Antibody The titer of the LIF-2 monoclonal antibody purified from the supernatant of the culture medium was detected by using indirect ELISA, and the specific steps were as follows:
(1) The LIF protein purified in Example 1 was coated on an ELISA plate at 2 μg/mL and 50 μL/well and incubated at 4° C. overnight.
(2) The coated plate was washed, 200 μL/well of PBS containing 2% BSA was added and blocked at 37° C. for 2 h.
(3) After the plate was washed, the LIF monoclonal antibody at a diluted concentration (diluted 1000 times, 2000 times, 4000 times, 8000 times, 16000 times, 32000 times, 64000 times, 128000 times, 256000 times, 512000 times, 1024000 times, 2048000 times, 4096000 times and 8192000 times) and PBS wells were added as a control, and incubated at 37° C. for 1 h.
(4) After the plate was washed, horseradish peroxidase-labeled goat anti-mouse antibody was added at 1:5000 times and incubated at 37° C. for 1 h.
(5) TMB chromogenic substrate (100 μL/well) was added thereto, and the reaction was performed for 5 min.
(6) The reaction was stopped by adding 50 μL of stop solution.
(7) OD values of the wells were read at 450 nm with a microplate reader, and the results are shown in Table 3.

As shown in Table 3, the LIF antibody titer purified from the supernatant of the culture medium was 106 or more, which indicates that the antibody titer is high.

TABLE 3

| Antibody titer | |
|---|---|
| Dilution factor of antibody | $OD_{450}$ |
| 1:1000 | 2.293 |
| 1:2000 | 2.076 |
| 1:4000 | 1.837 |
| 1:8000 | 1.818 |
| 1:16000 | 1.725 |
| 1:32000 | 1.454 |
| 1:64000 | 0.997 |
| 1:128000 | 0.78 |
| 1:256000 | 0.569 |
| 1:512000 | 0.379 |
| 1:1024000 | 0.219 |
| 1:2048000 | 0.149 |
| Blank control | 0.074 |

The obtained anti-giant panda LIF-2 monoclonal antibody is sent to General Biosystems (Anhui) Co., Ltd. for sequencing, and a heavy chain variable region sequence of the monoclonal antibody is as follows:

(SEQ ID NO. 1)
QVQLKQSGPSQVQPAQSLSMTCTVSGFSLTRYSVHWVRQSPGKGLEWLG
VIWKRGDTDYNAAFMSRLSITKDNSKSQVFFKMNSLQADDTAIYYCARK
RDGYSMDYWGQGTSVTVSS.

A light chain variable region sequence is as follows:

(SEQ ID NO. 2)
DVVMTQTPLSLPVSLGDQASISCRSSQSLVHSNGNTYLHWFLQKPGQSP
KLLIYKVSNRFSGVPDRFSGSGSGTDFTLKISRVEAEDLGVYLCSQSTH
VPWTFGGGTKLEIK.

In conclusion, the anti-giant panda LIF monoclonal antibody developed by the present invention can accurately identify the target protein LIF, and lays an important foundation for LIF protein localization, tissue expression information, study on LIF and a receptor and a target cell thereof by using the high-specificity LIF monoclonal antibody and exploration of the effect of LIF in embryonic diapause in giant pandas.

Finally, it should be noted that the foregoing embodiments are merely intended for illustrating the technical solutions of the present invention and do not limit the present invention. Although the present invention is described in detail with reference to the examples, those of ordinary skill in the art understand that the technical solutions of the present invention can be modified or equivalently substituted without departing from the essence and scope of the technical solutions of the present invention and should all be covered by the scope of the claims of the present invention.

What is claimed is:

1. An anti-giant panda LIF monoclonal antibody, comprising a heavy chain variable region having the amino acid sequence set forth in SEQ ID NO: 1 and a light chain variable region having the amino acid sequence set forth in SEQ ID NO: 2.

2. The anti-giant panda LIF monoclonal antibody according to claim 1, wherein the subtype of the anti-giant panda LIF monoclonal antibody is IgG2b.

3. An expression vector, comprising a nucleic acid encoding the anti-giant panda LIF monoclonal antibody according to claim 1.

4. A hybridoma cell line LIF-2 secreting the anti-giant panda LIF monoclonal antibody according to claim 1, wherein the hybridoma cell line is deposited at China Center for Type Culture Collection with the accession number of CCTCC NO: C202171.

* * * * *

SEQUENCE LISTING

```
Sequence total quantity: 7
SEQ ID NO: 1            moltype = AA  length = 117
FEATURE                 Location/Qualifiers
source                  1..117
                        mol_type = protein
                        organism = Synthetic construct
```

```
SEQUENCE: 1
QVQLKQSGPS QVQPAQSLSM TCTVSGFSLT RYSVHWVRQS PGKGLEWLGV IWKRGDTDYN     60
AAFMSRLSIT KDNSKSQVFF KMNSLQADDT AIYYCARKRD GYSMDYWGQG TSVTVSS       117

SEQ ID NO: 2            moltype = AA   length = 112
FEATURE                 Location/Qualifiers
source                  1..112
                        mol_type = protein
                        organism = Synthetic construct
SEQUENCE: 2
DVVMTQTPLS LPVSLGDQAS ISCRSSQSLV HSNGNTYLHW FLQKPGQSPK LLIYKVSNRF     60
SGVPDRFSGS GSGTDFTLKI SRVEAEDLGV YLCSQSTHVP WTFGGGTKLE IK            112

SEQ ID NO: 3            moltype = DNA   length = 351
FEATURE                 Location/Qualifiers
source                  1..351
                        mol_type = other DNA
                        organism = Synthetic construct
SEQUENCE: 3
caggtgcagc tgaagcagtc aggacctagc caagtgcagc ccgcacagag cctgtccatg     60
acctgcacag tctctggttt ctcattaact aggtatagtg tacactgggt tcgccagtct    120
ccaggaaagg gtctggagtg gctgggagtg atatgggaaa ggtggagaca agactacaat    180
gcagctttca tgtccagact gagcatcacc aaggacaact ccaaaagcca agttttcttt    240
aaaatgaaca gtctgcaagc tgatgacact gccatttact actgtgccag gaaaagggat    300
ggttattcta tggactactg gggtcaagga acctcagtca ccgtctcctc a             351

SEQ ID NO: 4            moltype = DNA   length = 336
FEATURE                 Location/Qualifiers
source                  1..336
                        mol_type = other DNA
                        organism = Synthetic construct
SEQUENCE: 4
gatgttgtga tgacccaaac tccactctcc ctgcctgtca gtcttggaga tcaagcctcc     60
atctcttgca gatctagtca gagccttgta cacagtaatg gaaacaccta tttacattgg    120
ttcctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatctctgct ctcaaagtac acatgttccg    300
tggacgttcg gtggaggcac caagctggaa atcaaa                              336

SEQ ID NO: 5            moltype = AA   length = 238
FEATURE                 Location/Qualifiers
source                  1..238
                        mol_type = protein
                        organism = Synthetic construct
SEQUENCE: 5
MKLPVRLLVL MFWIPASSSD VVMTQTPLSL PVSLGDQASI SCRSSQSLVH SNGNTYLHWF     60
LQKPGQSPKL LIYKVSNRFS GVPDRFSGSG SGTDFTLKIS RVEAEDLGVY LCSQSTHVPW    120
TFGGGTKLEI KRADAAPTVS IFPPSSEQLT SGGASVVCFL NNFYPKDINV KWKIDGSERQ    180
NGVLNSWTDQ DSKDSTYSMS STLTLTKDEY ERHNSYTCEA THKTSTSPIV KSFNRNEC      238

SEQ ID NO: 6            moltype = AA   length = 549
FEATURE                 Location/Qualifiers
source                  1..549
                        mol_type = protein
                        organism = Synthetic construct
SEQUENCE: 6
TTLDSQVFLF SDKHRNRTFT MYLGLNCVFI VFLLKGVQSQ VQLKQSGPSQ VQPAQSLSMT     60
CTVSGFSLTR YSVHWVRQSP GKGLEWLGVI WKRGDTDYNA AFMSRLSITK DNSKSQVFFK    120
MNSLQADDTA IYYCARKRDG YSMDYWGQGT SVTVSSAKTT PPSVYPLAPG SAAQTNSMVT    180
LGCLVKGYFP EPVTVTWNSG SLSSGVHTFP AVLQSDLYTL SSSVTVPSST WPSETVTCNV    240
AHPASSTKVD KKIVPRDCGC KPCICTVPEV SSVFIFPPKP KDVLTITLTP KVTCVVVDIS    300
KDDPEVQFSW FVDDVEVHTA QTQPREEQFN STFRSVSELP IMHQDWLNGK EFKCRVNSAA    360
FPAPIEKTIS KTKGRPKAPQ VYTIPPPKEQ MAKDKVSLTC MITDFFPEDI TVEWQWNGQP    420
AENYKNTQPI MDTDGSYFVY SKLNVQKSNW EAGNTFTCSV LHEGLHNHHT EKSLSHSPGL    480
QLDETCAEAQ DGELDGLWTT ITIFISLFLL SVCYSAAVTL FKVKWIFSSV VELKQTLVPE    540
YKNMIGQAP                                                           549

SEQ ID NO: 7            moltype = AA   length = 202
FEATURE                 Location/Qualifiers
source                  1..202
                        mol_type = protein
                        organism = Synthetic construct
SEQUENCE: 7
MKVLAAGVVP LLLVLHWKHG AGSPLPITPV NATCATRHPC HSNLMNQIRN QLAQLNGSAN     60
ALFILYYTAQ GEPFPNNLDK LCGPNVTDFP PFHANGTERT RLVELYRLIA YLGASLGNIT    120
RDQKVLNPNA LSLHSKLNAT ADIMRGLLSN VLCRLCNKYH VAHVDVAYGP DTSGKDVFQK    180
KKLGCQLLGK YKQVIAVVAQ AF                                             202
```